(12) United States Patent
Qu

(10) Patent No.: US 8,974,841 B2
(45) Date of Patent: Mar. 10, 2015

(54) CHINESE MEDICINAL COMPOSITIONS USEFUL AS ANTI-FATIGUE, ANTI-AGING AND GONADOTROPHIC AGENT AND PROCESSES FOR PREPARATION THEREOF

(76) Inventor: Shengbo Qu, Shanghai (CN)

( * ) Notice: Subject to any disclaimer, the term of this patent is extended or adjusted under 35 U.S.C. 154(b) by 632 days.

(21) Appl. No.: 12/089,438

(22) PCT Filed: Oct. 8, 2006

(86) PCT No.: PCT/CN2006/002610
§ 371 (c)(1),
(2), (4) Date: Apr. 7, 2008

(87) PCT Pub. No.: WO2007/041940
PCT Pub. Date: Apr. 19, 2007

(65) Prior Publication Data
US 2008/0241286 A1    Oct. 2, 2008

(30) Foreign Application Priority Data

Oct. 8, 2005 (CN) .......................... 2005 1 0030275

(51) Int. Cl.
*A61K 36/258* (2006.01)
*A61K 36/00* (2006.01)
*A61K 36/815* (2006.01)
*A61K 36/704* (2006.01)

(52) U.S. Cl.
CPC ............. *A61K 36/258* (2013.01); *A61K 36/704* (2013.01); *A61K 36/815* (2013.01)
USPC .......................................... 424/728; 424/725

(58) Field of Classification Search
None
See application file for complete search history.

(56) References Cited

FOREIGN PATENT DOCUMENTS

| CN | 1070576 A | * | 4/1993 |
| CN | 1123177 A | * | 5/1996 |
| CN | 1192915 A | * | 9/1998 |

OTHER PUBLICATIONS

Xiao et al, Immunological aspects of Chinese medicinal plants as antiageing drugs, Journal of Ethnopharmacology, 38 (1993) 167-175.*
Ohmori et al, Development and evaluation of the tablets coated with the novel formulation termed thin-layer sugarless coated tablets, International Journal of Pharmaceutics 278 (2004) 459-469.*

* cited by examiner

*Primary Examiner* — Qiuwen Mi
(74) *Attorney, Agent, or Firm* — Tianhua Gu; Global IP Services

(57) ABSTRACT

Chinese medicinal compositions useful as anti-fatigue, anti-aging and gonadotrophic agent and processes for preparation thereof, active ingredients of which being prepared from *Fructus lycii, Panax quinquefolium* and *Radices polygoni multiflor*. The present compositions are prepared by micronization of starting materials in their entirety.

2 Claims, No Drawings

CHINESE MEDICINAL COMPOSITIONS USEFUL AS ANTI-FATIGUE, ANTI-AGING AND GONADOTROPHIC AGENT AND PROCESSES FOR PREPARATION THEREOF

FIELD OF THE INVENTION

The invention is related to a traditional Chinese medicinal composition having sanatory functions such as anti-fatigue, anti-aging and improvement of sexual functions, and a process for preparing thereof.

BACKGROUND OF THE INVENTION

With the improvement of human spiritual civilization and material civilization, it is realized that keeping health is not only a means for the prophylaxis and the treatment of diseases but also a regimen for health cultivation and improvement of life-quality. Nutrition and health-care products possessing effects such as anti-fatigue, anti-aging and improving sexual functions are warmly welcomed by people. A lot of health-care products and invigorants, prepared on the base of traditional Chinese medicinal materials including natural animals and plants, come into being because of demand and enrich the market constantly. However, various varieties of raw material of the traditional Chinese medicine and complicated processes for the preparation thereof have influenced, to some extent, the development of new varieties of health-care products from Chinese medicinal material. Aiming at this problem, a traditional Chinese medicinal composition with a simple formula and a convenient process for preparing same are disclosed in the invention.

SUMMARY OF THE INVENTION

One purpose of the invention is to provide a traditional Chinese medicinal composition substantially comprises *Fructus lycii* (medlar), *Panax quinquefolium* (Root of American ginseng) and *Radix polygoni multiflor*. Said composition possesses health-care effects, such as anti-fatigue, anti-aging and improving sexual functions.

Another purpose of the invention is to provide a process for the preparation of the composition of the invention.

The technical solution of the invention is: a traditional Chinese medicinal composition useful as an anti-fatigue, an anti-aging and a gonadotrophic/sexual function improving agent comprising 10%~90% *Fructus lycii*, 5%~85% *Panax quinquefolium* and 5%~85% *Radix polygoni multiflor* by weight.

The traditional Chinese medicinal composition of the invention can be prepared using the following process: pulverizing *Fructus lycii* into fine powder at a lower temperature; and micronizing *Panax quinquefolium* and *Radix polygoni multiflor*, separately, into fine powder; then weighing the fine powder of *Fructus lycii*, *Panax quinquefolium* and *Radix polygoni multiflor* in the above ratio and mixing them uniformly, thus the traditional Chinese medicinal composition is prepared.

Various common correctants and excipients can be incorporated into the traditional Chinese medicinal composition of the invention, and the mixture, by using conventional technologies, can be prepared into various forms of health remedies or nutraceuticals, such as honeyed bolus, tablet, or slurry, sugarless or low sugar powder, granules, capsules or tablets, or oral solution, or cake shape.

DETAIL DESCRIPTION OF THE INVENTION

The invention is now described in further detail in examples.

*Fructus lycii* was transferred into a low-temperature-pulverizer after being precooled at a lower temperature, then pulverized into powder at a fineness of less than or equal to 100-300 meshes at the temperature of −100° C. *Panax quinquefolium* was pulverized into powder at the fineness of less than or equal to 100-300 meshes in a common pulverizer or an ultra-fine pulverizer. *Radix polygoni multiflor* was processed in a processing technology, then pulverized into powder at a fineness of less than or equal to 100-300 meshes in a common pulverizer or an ultra-fine pulverizer. The pulverized raw materials were mixed uniformly and prepared into the traditional Chinese medicinal composition of the invention comprising 50% *Fructus lycii*, 25% *Panax quinquefolium* and 25% *Radix polygoni multiflor* by weight. In order to ensure the mixing uniform and to avoid the gluing of the powder of *Fructus lycii*, the mixing process must also be completed at a lower temperature.

It is shown, in the present studies, that the traditional rare medicinal material in China, *Fructus lycii*, contains a lot of active components such as medlar polysaccharide, betaine, scopolamine, thiamine, lactoflavin, sterine, cinnamoylhistamine, eldrin, medlar leaf protein, a variety of amino acids and trace elements, etc., and that *Fructus lycii* possesses effects of enhancing immunity, controlling glycemia, reducing lipids, decreasing blood pressure, protecting hepatocytes and renal cells, and anti-aging and anti-tumor. It is presumed, in theories of traditional Chinese medicine, that the efficacies of *Fructus lycii* are nourishing the liver and kidney, promoting essence production, improving eyesight, and *Fructus lycii* can be used for the treatment of kidney-essence deficiency, lumbago, Vertigo and tinnitus, calor intemus and diabetes, hemopenia and etiolate, and hypopsia.

*Panax quinquefolium* is cold-natured, bitter in taste with tiny sweet, and is directed to heat meridian, the lung meridian and Shenjing point (renal meridian). Its efficacies are invigorating QI (invigorating vital energy), nourishing YIN, reducing internal heat, and promoting the production of body fluid. The primary pharmacological components of *Panax quinquefolium* are total saponins of *Panax quinquefolium*, which are effective in improving myocardial function, anti-ischemic, anti-arrhythmia, anti-stock, and resisting arteriosclerosis. Taking *Panax quinquefolium* may strengthen physique, improve immunity, resist anoxia, resist fatigue, stand out high temperature, cold and thirst and hunger. Furthermore, *Panax quinquefolium* possesses efficacies of promoting hemopoietic ability and controlling glycemia.

*Radix polygoni multiflori* contains anthraquinones, lecithin, starch and crude fat, etc. It has been shown, in pharmacological experiments, that *Radix polygoni multiflori* possesses actions of enhancing heart function, reducing lipids, decreasing blood pressure, improving immunity and promoting hemopoietic ability. There are two kinds of *Radix polygoni multiflori*, Raw *Radix Polygoni Multiflori* and *Radix Polygoni Multiflori Preparata* (processed *Radix polygoni Multiflori*). *Radix Polygoni Multiflori Preparata* is a good anti-fatigue and anti-aging medicine due to its efficiencies in tonifying liver and kidney, nourishing essence and blood, darkening beard and hair, and strengthening bone and musculature. It is often used for the treatment of vertigo and tinnitus, early whiten beard and hair, lumbar debility, limb anaesth, neurasthenia and hyperlipoidemia.

The traditional Chinese medicinal composition of the invention, comprising *Fructus lycii* (medlar), *Panax quinquefolium* (Root of American ginseng) and *Radix polygoni multiflor* as basic components, has shown efficacies of enhancing the health, anti-fatigue and anti-aging. According to the theories of the traditional Chinese medicine, the primary reasons of sexual dysfunction are hepatic asthenia and sukra prameha and deficiency of kidney-QI. The traditional Chinese medicinal composition of the invention possesses efficacies of nourishing liver and kidney, and nourishing blood and essence. It can be used to improve male and female sexual dysfunction, enhance libido, induce sexual excitement and improve the quality of sexual life.

The traditional Chinese medicinal composition of the invention is prepared by micronization of all starting materials, so that effective ingredients are absorbed thoroughly and utilized completely, and the cost of production can be decreased obviously.

Example 1

A sufficient quantity of honey was added into the traditional Chinese medicinal composition of the invention as an excipient and corrective, and the mixture was made into a form of honeyed bolus, tablet or slurry by using common technical means. The dosage of the Chinese medicinal composition for oral administration is 15-30 g per day.

Example 2

The traditional Chinese medicinal composition of the invention was made into sugarless or low sugar powder, granules, capsules or tablets, without adding any sugary excipient or corrective, by using common technical means. The dosage of the Chinese medicinal composition for oral administration is 15-30 g a day.

Example 3

Black sesame powder, walnut powder, starch, protein powder or grain dust, or a mixture of one or more substances selected from the above was added into the traditional Chinese medicinal composition of the invention, then, the mixture was made into nutritions and health-care products in form of oral solution or cake. The dosage of the Chinese medicinal composition for oral administration is 15-30 g per day.

What is claimed is:

1. A method of improving gonadotrophic/sexual function, comprising: oral administering a daily dosage of a traditional Chinese medicinal composition to a patient suffering from gonadotrophic/sexual dysfunction, wherein said daily dosage comprises about 15-30 g of the Chinese medicinal composition comprising 10%~90% *Fructus lycii*, 5%~85% *Panax quinquefolium* and 5%~85% *Radix polygoni multiflor*, by weight.

2. The method of improving gonadotrophic/sexual function according to claim 1, wherein said Chinese medicinal composition comprising 50% *Fructus lycii* powder, 25% *Panax quinquefolium* and 25% *Radix polygoni multiflor*, by weight.

* * * * *